United States Patent
Jang et al.

(10) Patent No.: US 10,730,829 B2
(45) Date of Patent: Aug. 4, 2020

(54) COMPOUND EXHIBITING ANTI-OXIDATIVE OR ANTI-INFLAMMATORY ACTIVITY

(71) Applicant: University-Industry Cooperation Group of Kyung Hee University, Gyeonggi-do (KR)

(72) Inventors: Young Pyo Jang, Seoul (KR); Sang Cheol Park, Seoul (KR)

(73) Assignee: University-Industry Cooperation Group of Kyung Hee University, Gyeonggi-Do (KR)

(*) Notice: Subject to any disclaimer, the term of this patent is extended or adjusted under 35 U.S.C. 154(b) by 0 days.

(21) Appl. No.: 16/324,356

(22) PCT Filed: Aug. 10, 2017

(86) PCT No.: PCT/KR2017/008693
§ 371 (c)(1),
(2) Date: Feb. 8, 2019

(87) PCT Pub. No.: WO2018/030816
PCT Pub. Date: Feb. 15, 2018

(65) Prior Publication Data
US 2019/0218178 A1  Jul. 18, 2019

(30) Foreign Application Priority Data

Aug. 10, 2016 (KR) .................. 10-2016-0101899

(51) Int. Cl.
| | | |
|---|---|---|
| *C07C 323/52* | (2006.01) | |
| *A61K 31/195* | (2006.01) | |
| *A23L 33/10* | (2016.01) | |
| *A61K 31/18* | (2006.01) | |
| *C07C 323/25* | (2006.01) | |
| *C07C 323/59* | (2006.01) | |
| *A61K 8/44* | (2006.01) | |
| *A61Q 19/00* | (2006.01) | |
| *A61P 39/06* | (2006.01) | |
| *A61P 29/00* | (2006.01) | |
| *C07C 319/22* | (2006.01) | |

(52) U.S. Cl.
CPC ............ *C07C 323/52* (2013.01); *A23L 33/10* (2016.08); *A61K 8/44* (2013.01); *A61K 31/18* (2013.01); *A61K 31/195* (2013.01); *A61P 29/00* (2018.01); *A61P 39/06* (2018.01); *A61Q 19/00* (2013.01); *C07C 319/22* (2013.01); *C07C 323/25* (2013.01); *C07C 323/59* (2013.01); *A23V 2002/00* (2013.01); *Y02P 20/55* (2015.11)

(58) Field of Classification Search
CPC ........................... C07C 323/52; A61K 31/195
See application file for complete search history.

(56) References Cited

U.S. PATENT DOCUMENTS 3,448,141 A   6/1969   Marinier
4,331,656 A   5/1982   Bouillon et al.

OTHER PUBLICATIONS

Uttara, Oxidative Stress and Neurodegenerative Diseases: A Review of Upstream and Downstream Antioxidant Therapeutic Options, 2009, Current Neuropharmacology, vol. 7, p. 65-74. (Year: 2009).*
Galvez-Llompart et al "Modeling Natural Anti-Inflammatory Compounds by Molecular Topology" International Journal of Molecular Sciences vol. 12, pp. 9481-9503, 2011.
Kireche et al "Preservatives in Cosmetics: Reactivity of Allergenic Formaldehyde-Releasers Towards Amino Acids Through Breakdown Products Other Than Formaldehyde" Contact Dermatitis vol. 63, pp. 192-202, 2010.
Wang et al "A Thiol-Ene Coupling Approach to Native Peptide Stapling and Macrocyclization" Angewandte Chemie International Edition vol. 54, pp. 10931-10934, 2015.

* cited by examiner

*Primary Examiner* — Karen Cheng
(74) *Attorney, Agent, or Firm* — Cesari and McKenna, LLP

(57) ABSTRACT

The present invention relates to a novel compound exhibiting anti-oxidative or anti-inflammatory activity, a method of preparing the compound, a pharmaceutical composition for preventing or treating inflammatory diseases or the diseases caused by oxidation, which comprises the compound or a salt thereof as an active ingredient, and an anti-inflammatory or anti-oxidative cosmetic composition or food composition.

10 Claims, 11 Drawing Sheets

[FIG. 1]
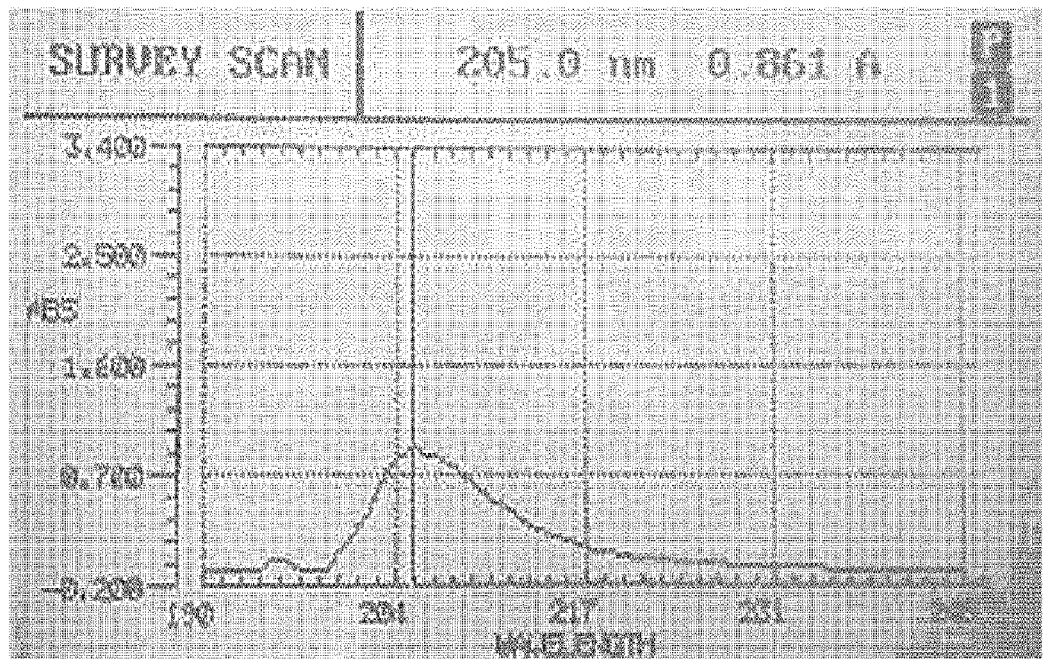
[FIG. 2]
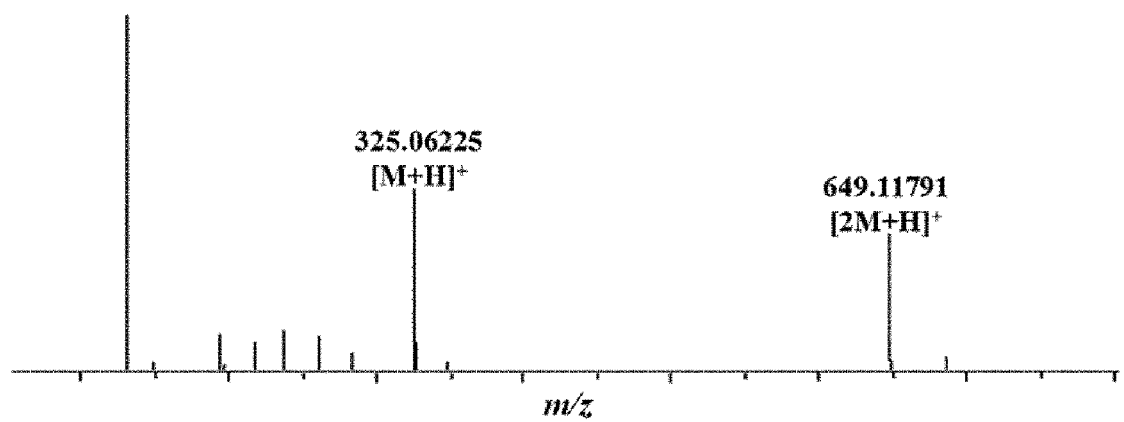

[FIG. 3]
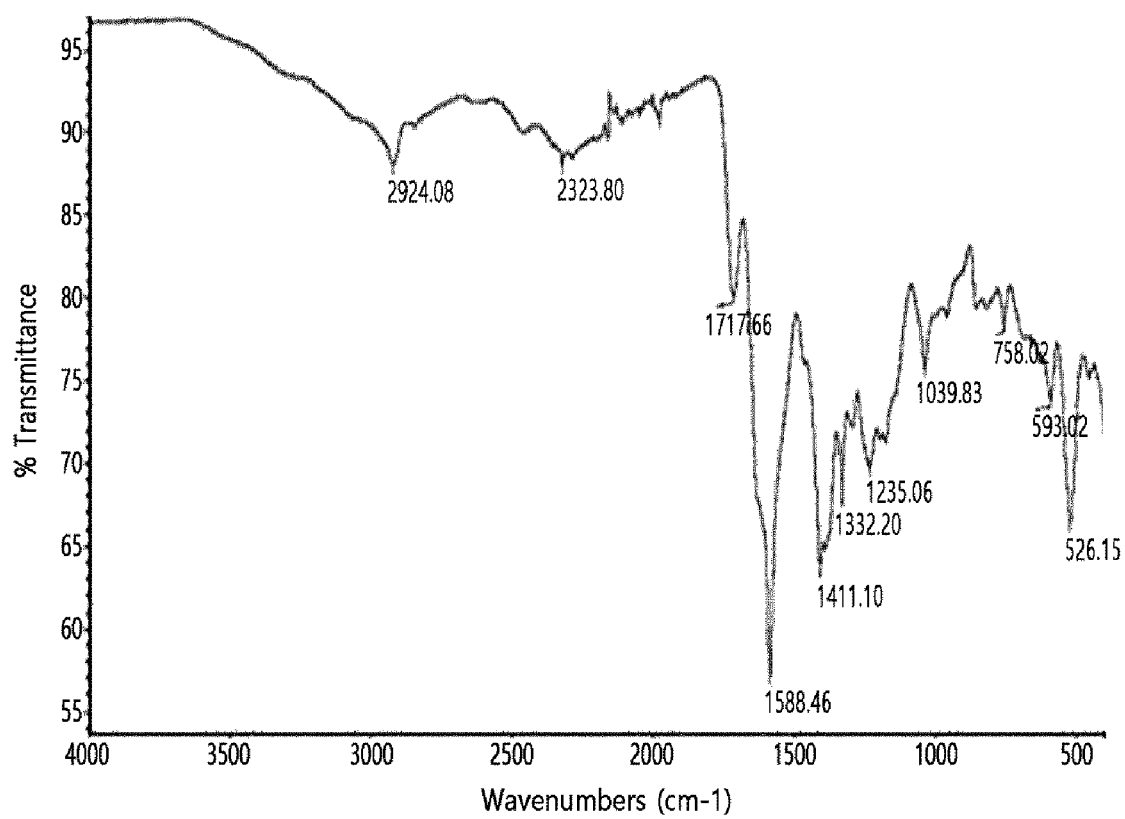

[FIG. 4]
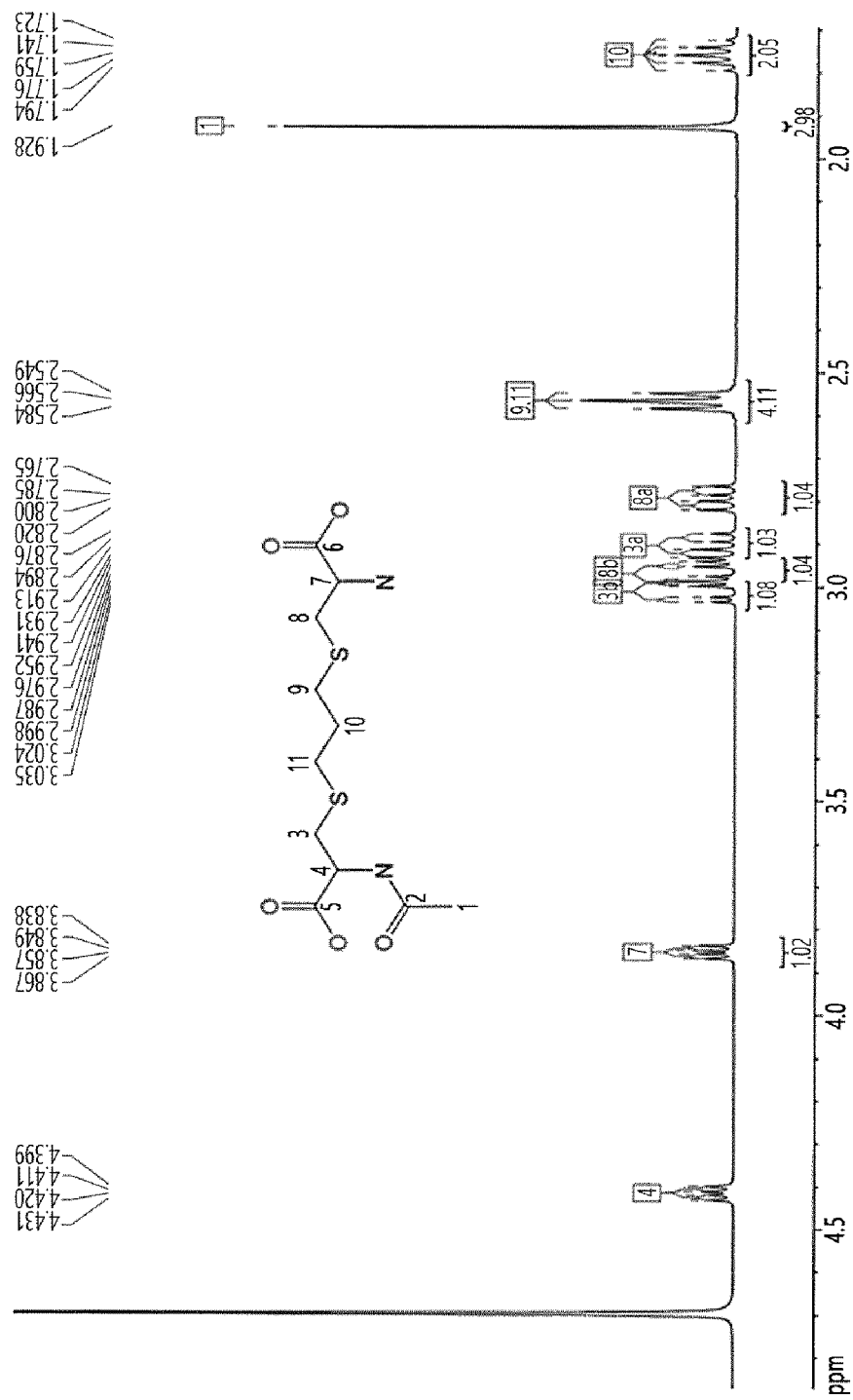

[FIG. 5]
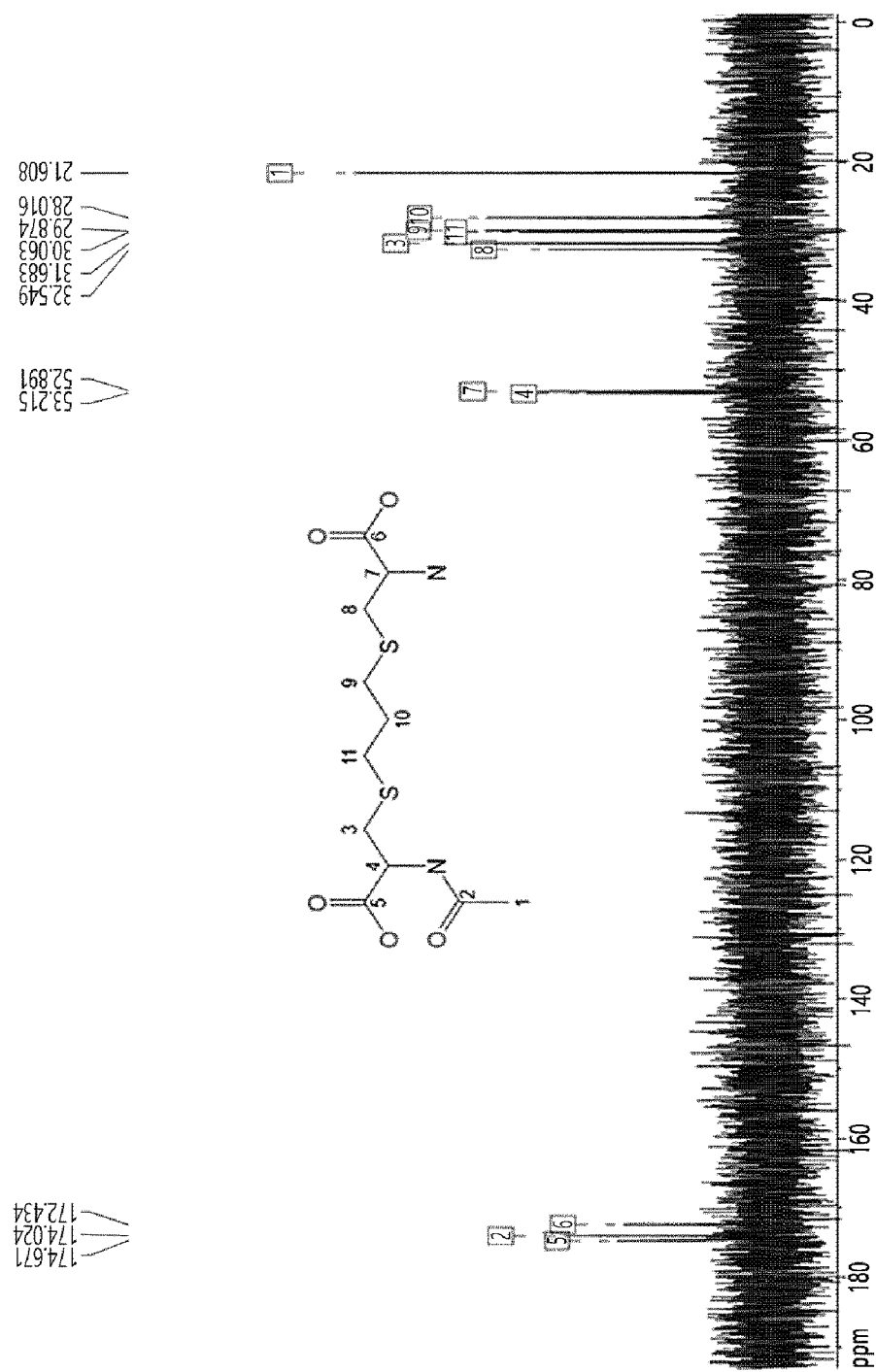

[FIG. 6]
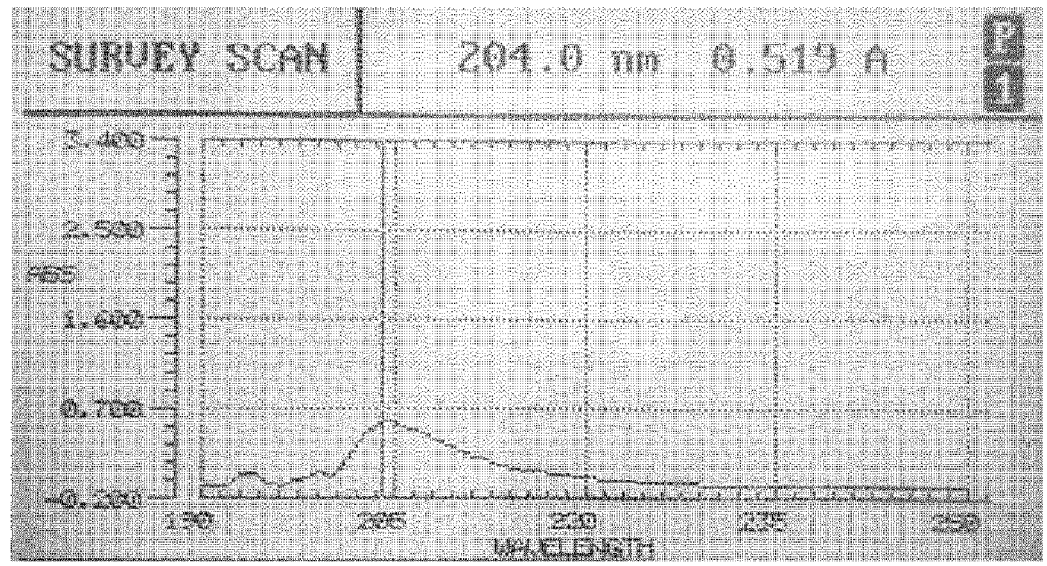
[FIG. 7]
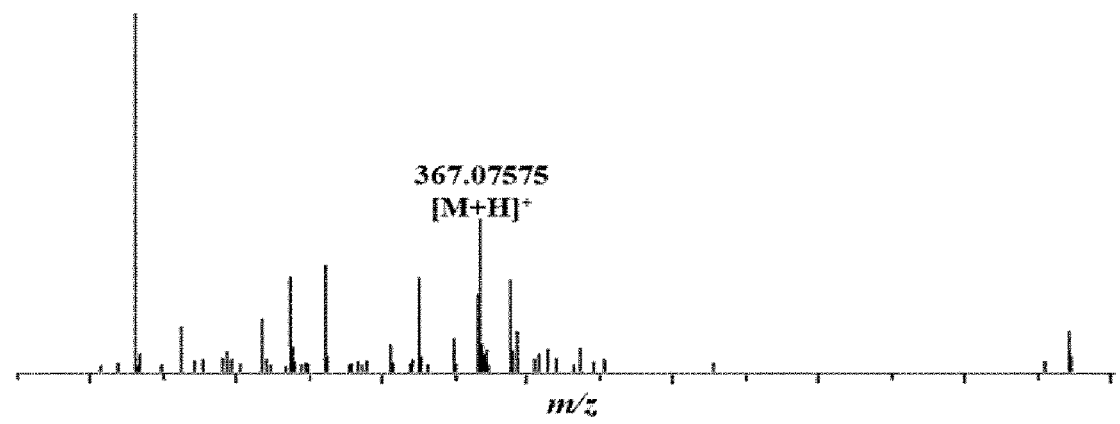

[FIG. 8]
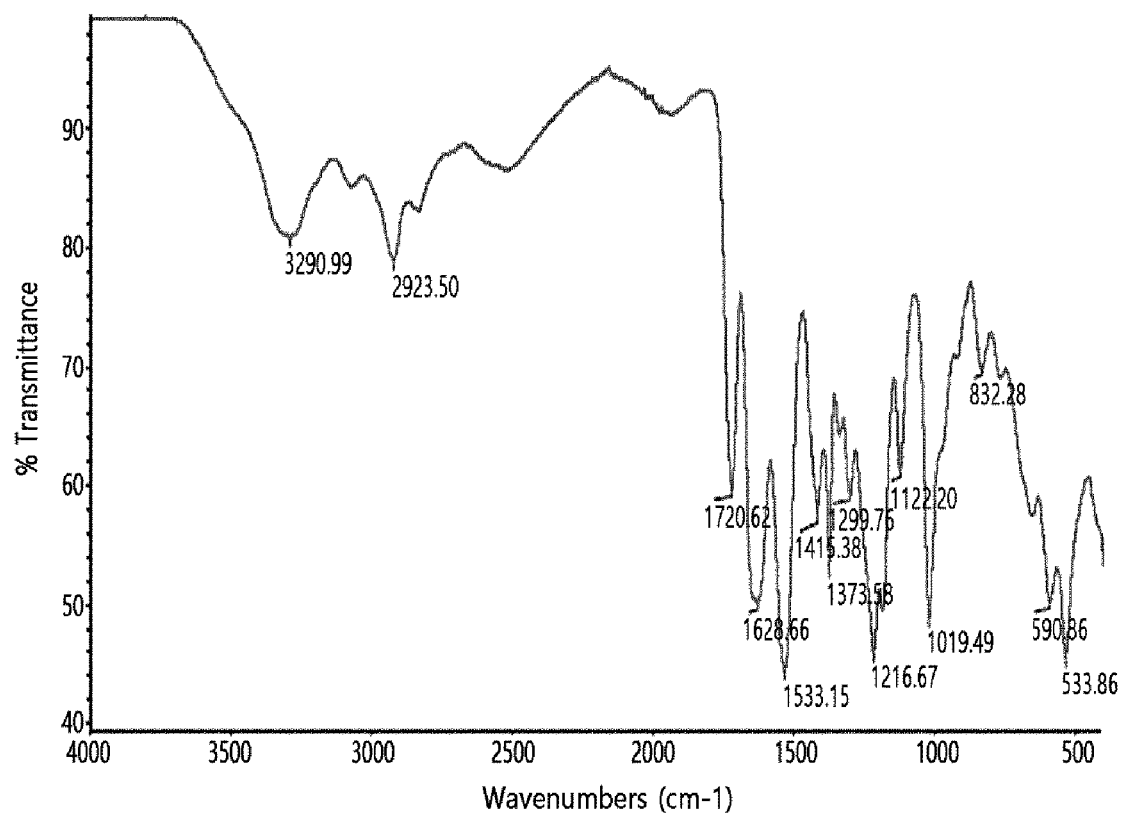

[FIG. 9]
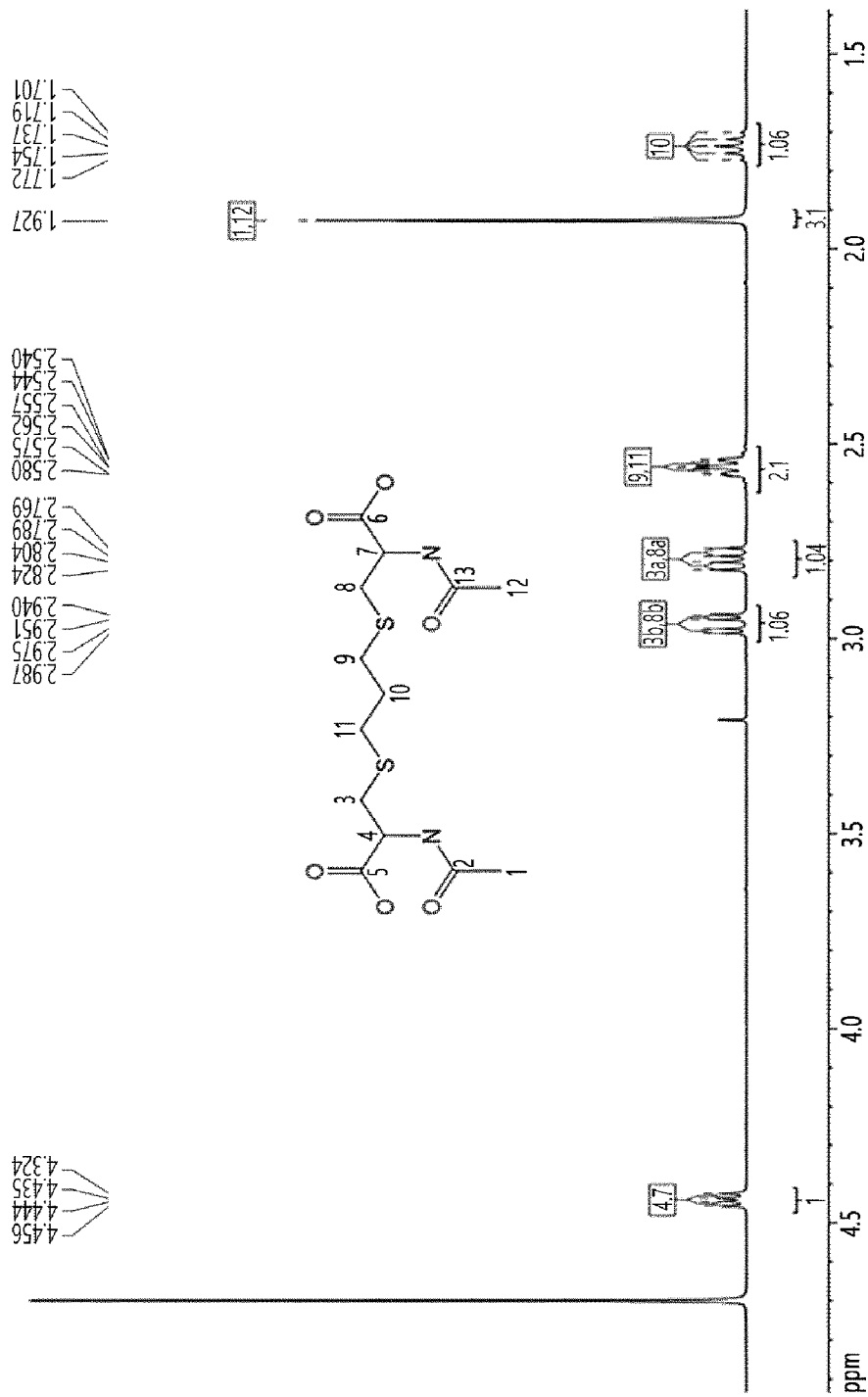

[FIG. 10]
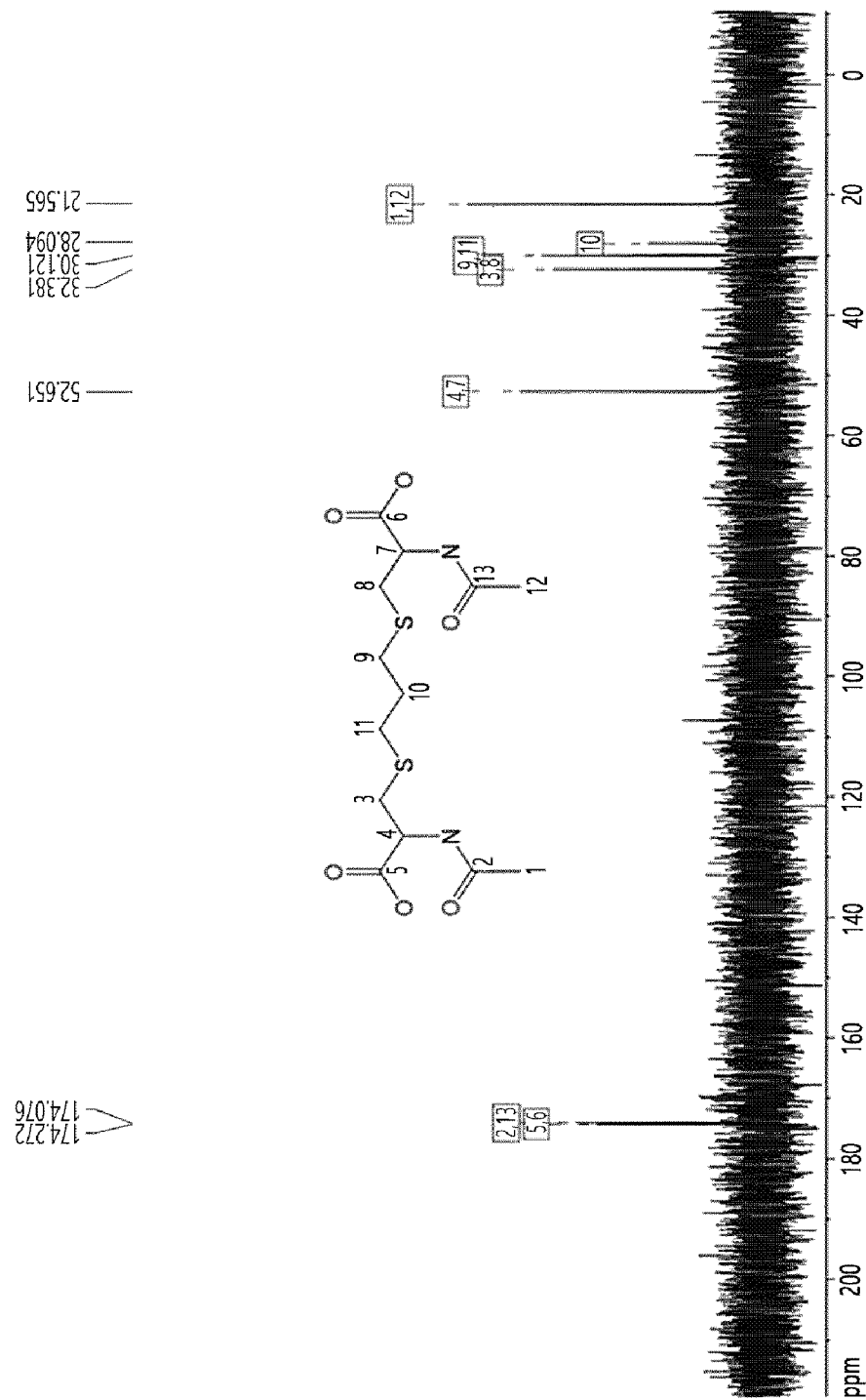

[FIG. 11]
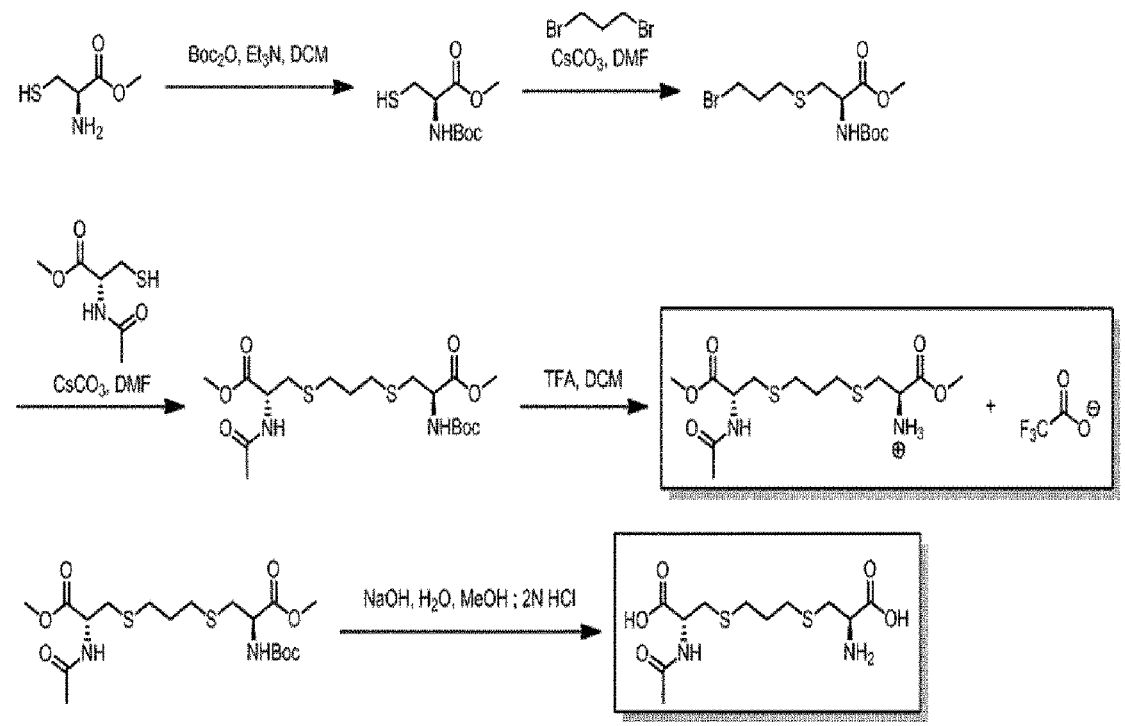

[FIG. 12]
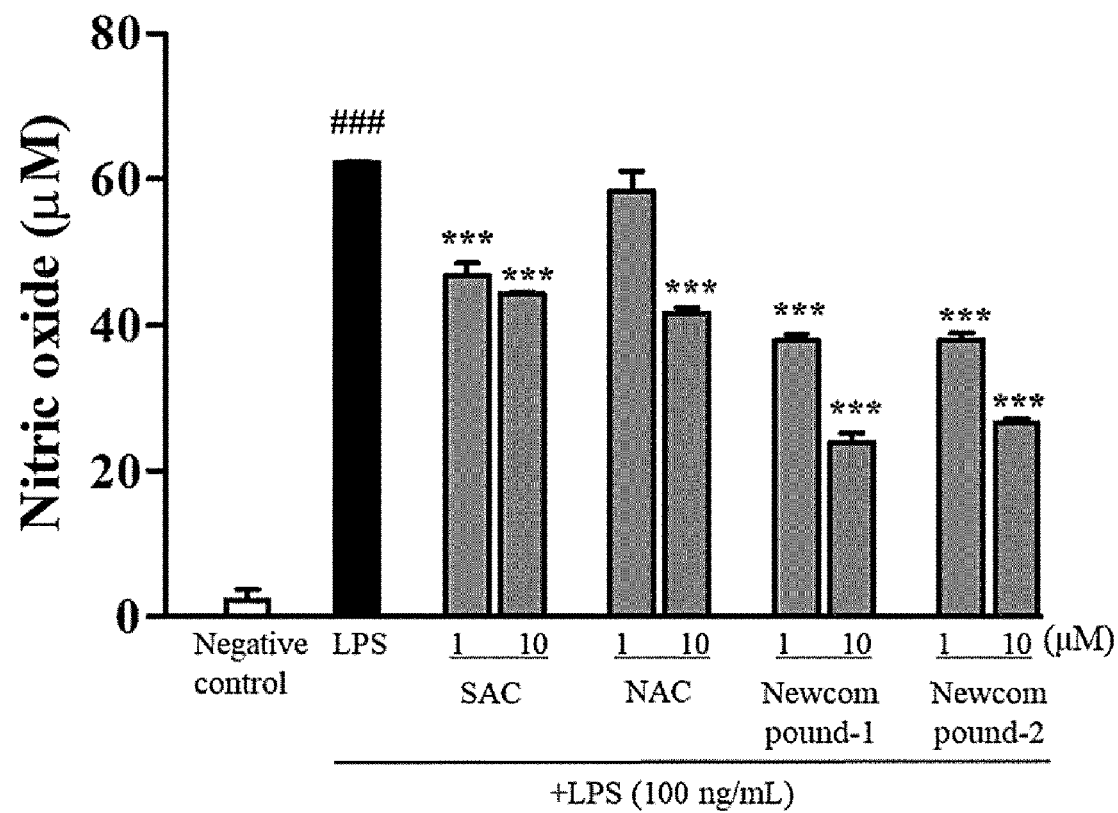

[FIG. 13]
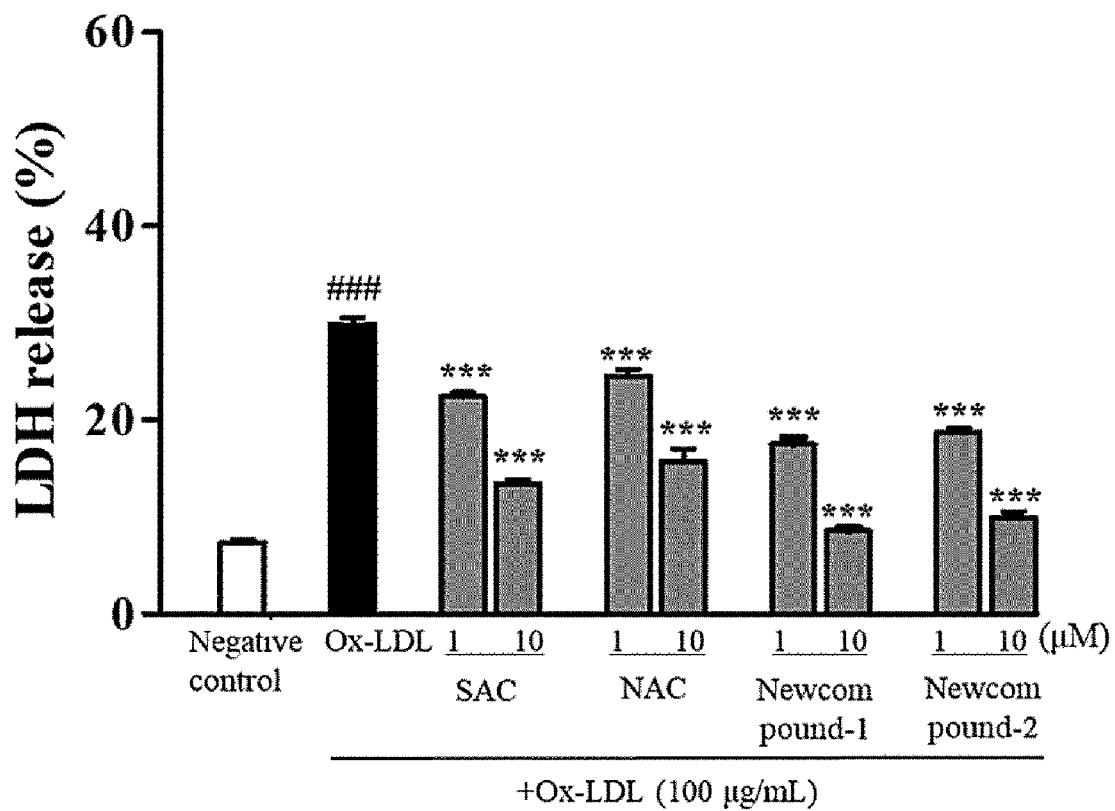

COMPOUND EXHIBITING ANTI-OXIDATIVE OR ANTI-INFLAMMATORY ACTIVITY

CROSS-REFERENCE TO RELATED APPLICATIONS

This application is the National Stage of International Application No. PCT/KR2017/008693, filed on Aug. 10, 2017, which claims priority to Korean Application No. 10-2016-0101899, filed on Aug. 10, 2016. The contents of both applications are hereby incorporated by reference in their entirety.

TECHNICAL FIELD

The present invention relates to a novel compound exhibiting an anti-oxidative or anti-inflammatory activity, a method of preparing the compound, a pharmaceutical composition for preventing or treating inflammatory diseases or the diseases caused by oxidation, which contains the compound or a salt thereof as an active ingredient, and an anti-inflammatory or anti-oxidative cosmetic composition or food composition.

BACKGROUND ART

The human body maintains a balance between oxidation promoting materials and oxidation inhibiting materials. However, when the body loses this balance and is inclined to a direction to promote oxidation due to various factors, oxidative stress is induced in the body to damage cells and cause pathological diseases. The reactive oxygen species (ROS), which is a direct cause of the oxidative stress, are chemically unstable and highly reactive, and thus they can easily react with various biomaterials (e.g., DNA, proteins, lipids, and carbohydrates) and attack the polymers in the body, thereby causing irreversible damage to cells and tissues or causing mutation, cytotoxicity, cancer, etc.

Meanwhile, macrophages in the human body produce inducers of inflammation (e.g., tumor necrotic factor-α (TNF-α), interleukin-6 (IL-6), interleukin-1β (IL-1β), etc.) by responding to pathogens, and produce nitric oxide (NO) and prostaglandins (prostaglandin E2, PGE2) by synthesizing cyclooxygenase-2 (iNOS) and cyclooxygenase-2 (COX-2). Physiologically, nitric oxide (NO) has various roles in removing bacteria and tumors, regulating blood pressure, mediating neurotransmission, etc. However, when an inflammatory reaction occurs, the expression of iNOS in the related cells increases and thus a large amount of NO is produced, and the excessively produced NO induces tissue damage, gene mutation, nerve damage, etc., and increases vascular permeability to promote inflammatory reactions (e.g., edema, etc.).

When an inflammatory reaction occurs, various free radicals are produced along with various inducers of inflammation. Normal free radicals are involved in the maintenance of cell homeostasis and affect differentiation, growth, survival, and aging of cells. Among these free radicals, reactive oxygen species (ROS) are produced in the mitochondria in a cell through the oxidation and reduction of oxygen by respiration and immune responses. Harmful ROS are generally removed by the actions of anti-oxidant systems (e.g., superoxide dismutase, catalase, glutathione peroxidase, glutamine reductase, vitamin C, vitamin E, uric acid, and bilirubin). However, when the balance between the generation and removal of free radicals collapses, it results in generation of oxidative stress thereby causing various pathological changes (e.g., inflammation, aging, cancer, etc.). In fact, it has been shown that oxidative stress is increased in many clinical diseases, and various studies have been conducted on new anti-oxidants to reduce such oxidative stress.

In this regard, the present inventors have made efforts to discover a novel compound with ensured safety and improved anti-oxidative and anti-inflammatory effects using a safe and effective compound derived from a natural material. As a result, they have confirmed that the compounds which were synthesized using S-allyl-L-cysteine and N-acetyl-L-cysteine as reactants exhibit more excellent safety as well as anti-oxidative and anti-inflammatory activities compared to those of the reactants, thereby completing the present invention.

DISCLOSURE

Technical Problem

An object of the present invention is to provide a novel compound or a pharmaceutically acceptable salt thereof that exhibits an anti-inflammatory or anti-oxidative activity.

Another object of the present invention is to provide a method for preparing the compound of the present invention, which includes reacting S-allyl-L-cysteine and N-acetyl-L-cysteine by ultraviolet irradiation of an aqueous solution containing the S-allyl-L-cysteine and N-acetyl-L-cysteine.

Still another object of the present invention is to provide a method for preparing the compound of the present invention, which includes (a) introducing a protecting group into the amine group of the L-cysteine methyl ester; (b) reacting the product of Step (a) with 1,3-dihalopropane; and (c) reacting the product of Step (b) with N-acetyl-L-cysteine methyl ester.

Still another object of the present invention is to provide a pharmaceutical composition for preventing or treating inflammatory diseases, which contains the compound of the present invention or a pharmaceutically acceptable salt thereof as an active ingredient.

Still another object of the present invention is to provide a pharmaceutical composition for preventing or treating the diseases caused by oxidation, which contains the compound of the present invention or a pharmaceutically acceptable salt thereof as an active ingredient.

Still another object of the present invention is to provide a method for preventing or treating inflammatory diseases or the diseases caused by oxidation, which includes administering the pharmaceutical composition to a subject in need thereof.

Still another object of the present invention is to provide an anti-inflammatory or anti-oxidative cosmetic composition, which contains the compound of the present invention or a cosmetically acceptable salt thereof as an active ingredient.

Still another object of the present invention is to provide an anti-inflammatory or anti-oxidative food composition, which contains the compound of the present invention or a sitologically acceptable salt thereof as an active ingredient.

Technical Solution

The present inventors, while making efforts to discover a novel compound with ensured safety and improved anti-oxidative and anti-inflammatory effects using a safe and effective compound derived from a natural material, have confirmed that the compounds which were synthesized using S-allyl-L-cysteine and N-acetyl-L-cysteine as reactants exhibit more excellent safety as well as anti-oxidative and anti-inflammatory activities compared to those of the reactants, and thereby completed the present invention.

Advantageous Effects of the Invention

The novel compounds with an anti-inflammatory or anti-oxidative effect of the present invention were synthesized based on compounds derived from natural materials and their safety was confirmed. Since these compounds exhibit excellent pharmacological activity compared to that of the reactants, they can be used for anti-inflammatory or anti-oxidative use. Accordingly, the novel compounds with an anti-inflammatory or anti-oxidative effect of the present invention can be effectively used not only as a pharmaceutical composition for preventing or treating inflammatory diseases or the diseases caused by oxidation, but also as an anti-inflammatory or anti-oxidative cosmetic composition or food composition.

BRIEF DESCRIPTION OF DRAWINGS

FIG. 1 shows the UV-Vis absorption spectrum of 2-acetamido-3-(3-(2-amino-2-carboxyethylthio)propylthio)propanoic acid synthesized according to an embodiment of the present invention.

FIG. 2 shows the UPCL-ESI-MS spectrum of 2-acetamido-3-(3-(2-amino-2-carboxyethylthio)propylthio)propanoic acid synthesized according to an embodiment of the present invention.

FIG. 3 shows the IR spectrum of 2-acetamido-3-(3-(2-amino-2-carboxyethylthio)propylthio)propanoic acid synthesized according to an embodiment of the present invention.

FIG. 4 shows the $^1$H-NMR spectrum, measured in $D_2O$, of 2-acetamido-3-(3-(2-amino-2-carboxyethylthio)propylthio)propanoic acid synthesized according to an embodiment of the present invention.

FIG. 5 shows the $^{13}$C-NMR spectrum, measured in $D_2O$, of 2-acetamido-3-(3-(2-amino-2-carboxyethylthio)propylthio)propanoic acid synthesized according to an embodiment of the present invention.

FIG. 6 shows the UV-Vis absorption spectrum of 2,14-dioxo-6,10-dithia-3,13-diazapentadecan-4,12-dicarboxylic acid synthesized according to an embodiment of the present invention.

FIG. 7 shows the UPCL-ESI-MS spectrum of 2,14-dioxo-6,10-dithia-3,13-diazapentadecan-4,12-dicarboxylic acid synthesized according to an embodiment of the present invention.

FIG. 8 shows the IR spectrum of 2,14-dioxo-6,10-dithia-3,13-diazapentadecan-4,12-dicarboxylic acid synthesized according to an embodiment of the present invention.

FIG. 9 shows the $^1$H-NMR spectrum, measured in $D_2O$, of 2,14-dioxo-6,10-dithia-3,13-diazapentadecan-4,12-dicarboxylic acid synthesized according to an embodiment of the present invention.

FIG. 10 shows the $^{13}$C-NMR spectrum, measured in $D_2O$, of 2,14-dioxo-6,10-dithia-3,13-diazapentadecan-4,12-dicarboxylic acid synthesized according to an embodiment of the present invention.

FIG. 11 shows the entire reaction scheme of a method for preparing a compound according to an embodiment of the present invention.

FIG. 12 shows a graph illustrating the inhibitory effect on nitric oxide production by the compounds according to embodiments of the present invention, in which the untreated group was used as the negative group, the group treated with lipopolysaccharide (LPS) was used as the positive group, and the groups treated with each of S-allyl-L-cysteine and N-acetyl-L-cysteine (which were used as reactants) were used as comparative examples.

FIG. 13 shows a graph illustrating the inhibitory effect on lactate dehydrogenase (LDH) release rate by the compounds according to embodiments of the present invention, in which the untreated group was used as the negative group, the group treated with oxidized low density lipoprotein (Ox-LDL) was used as the positive group, and the groups treated with each of S-allyl-L-cysteine and N-acetyl-L-cysteine (which were used as reactants) were used as comparative examples.

BEST MODE

To achieve the above objects, an aspect of the present invention provides a compound of the following Formula 1, an isomer thereof, or a pharmaceutically acceptable salt of the compound or its isomer:

[Formula 1]

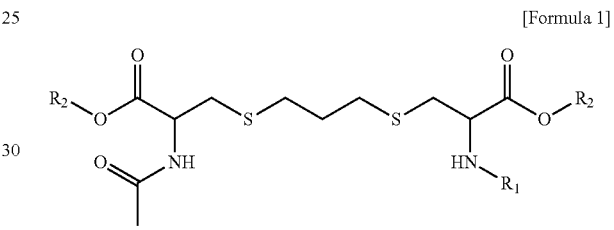

in which, in Formula 1 above,
$R_1$ is hydrogen or acetyl; and
$R_2$ is hydrogen or methyl.

In addition, the present invention provides a method for preparing the compound of Formula 1 above, which includes reacting S-allyl-L-cysteine and N-acetyl-L-cysteine by ultraviolet irradiation of an aqueous solution containing S-allyl-L-cysteine and N-acetyl-L-cysteine.

The ultraviolet rays irradiated for the reaction may be light with a wavelength in the range of 330 nm to 400 nm.

The reaction may be performed at 15° C. to 35° C., but the reaction temperature is not limited thereto.

In particular, S-allyl-L-cysteine and N-acetyl-L-cysteine may be reacted in a molar ratio of 1:0.7 to 1:1.3. For example, in a specific embodiment of the present invention, the two kinds of reactants were reacted in the same equivalent to synthesize the compound of the present invention.

Additionally, the present invention provides a method for preparing the compound of Formula 1 above, which includes (a) introducing a protecting group into the amine group of the L-cysteine methyl ester; (b) reacting the product of Step (a) with 1,3-dihalopropane; and (c) reacting the product of Step (b) with N-acetyl-L-cysteine methyl ester.

In the above reaction, the N-acetyl-L-cysteine methyl ester may be produced via methyl esterification of N-acetyl-L-cysteine.

In the above reaction, (d) deprotecting the amine group may be included after Step (c).

In the above reaction, the deprotection of Step (d) may be performed by sequentially reacting with a base and an acid.

Furthermore, the present invention provides a pharmaceutical composition for preventing or treating inflammatory diseases, which contains a compound of Formula 1 above, an isomer thereof, or a pharmaceutically acceptable salt of the compound or its isomer as an active ingredient.

The inflammatory disease that can be prevented or treated using the compound of the present invention is a generic term for diseases with inflammation as the main lesion, and may include allergic diseases comprising allergic asthma, allergic rhinitis, allergic mucositis, urticaria, and anaphylaxis; myopathy comprising systemic sclerosis, dermatomyositis, and inclusion body myositis; arthritis; atopic dermatitis; psoriasis; asthma; multiple sclerosis; ssRNA and dsRNA virus infection; sepsis; multiple chondritis; scleroderma; eczema; gout; periodontal disease; Behcet's syndrome; edema; vasculitis; Kawasaki disease; diabetic retinitis; autoimmune pancreatitis; vasculitis; glomerulonephritis; acute and chronic bronchitis; and influenza infection, but the diseases are not limited thereto.

Additionally, the present invention provides a pharmaceutical composition for preventing or treating diseases caused by oxidation, which contains a compound of Formula 1 above, an isomer thereof, or a pharmaceutically acceptable salt of the compound or its isomer as an active ingredient.

The diseases caused by oxidation which can be prevented or treated using the compound of the present invention may be, for example, those diseases which occur by reactive oxygen species (ROS). Examples of the diseases caused by reactive oxygen species (ROS) may include various diseases, such as degenerative neurological diseases including arteriosclerosis, Lou Gehrig's disease, Parkinson's disease, Alzheimer's disease, amyotrophic lateral sclerosis, and Huntington's disease; cardiovascular diseases including myocardial infarction, angina pectoris, coronary artery disease, and ischemic heart disease; ischemic brain diseases including stroke; diabetes; gastrointestinal diseases including gastritis and gastric cancer; cancer; leukemia; aging; rheumatoid arthritis; hepatitis; and atopic dermatitis, but the diseases are not limited thereto, and the disease may be aging that occurs by reactive oxygen species (ROS).

As used herein, the term "prevention" refers to all activities that inhibit or delay the onset, spread, and recurrence of inflammatory diseases or diseases caused by oxidation through the administration of the composition of the present invention, and the term "treatment" refers to all activities that improve or advantageously change the symptoms of the above diseases by administering the composition of the present invention.

The composition of the present invention can inhibit the production of nitrogen oxides and/or release of lactate dehydrogenase (LDH), and thus can be effectively used for the prevention and treatment of diseases induced by oxidation.

For example, the composition of the present invention may be formulated into various forms including oral preparations (e.g., powders, granules, tablets, capsules, suspensions, emulsions, syrups, aerosols, etc.), sterile injection solutions, etc., according to the conventional methods for each purpose of use. The composition of the present invention may be administered orally or administered via various routes (e.g., intravenous, intraperitoneal, subcutaneous, rectal, topical administrations, etc.). Examples of appropriate carriers, excipients, or diluents to be contained in the composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, mineral oil, etc. In addition, the composition of the present invention may further contain fillers, anti-coagulants, lubricants, humectants, fragrances, emulsifiers, preservatives, etc.).

Examples of solid preparations for oral administration may include tablets, pills, powders, granules, capsules, etc. These solid preparations may be formulated, for example, by addition of at least one excipient (e.g., starch, calcium carbonate, sucrose, lactose, gelatin, etc.) to the composition. In addition, lubricants (e.g., magnesium stearate, talc, etc.) may be used in addition to the simple excipients.

Examples of liquid preparations for oral administration may include suspensions, preparations for internal use, emulsions, syrups, etc., and various kinds of excipients (e.g., humectants, sweeteners, fragrances, preservatives, etc.) may be included in addition to simple diluents (i.e., water and liquid paraffin).

Examples of parenteral preparations may include sterile aqueous solutions, non-aqueous solutions, suspensions, emulsions, lyophilized preparations, and suppositories. Examples of the non-aqueous solvents or suspending agents may include propylene glycol, polyethylene glycol, vegetable oil (e.g., olive oil), injectable ester (e.g., ethyl oleate), etc. Examples of the bases for the suppositories may include witepsol, macrogol, Tween 61, cacao butter, Laurin, glycerogelatine, etc. Meanwhile, for the injections, conventional additives (e.g., solubilizers, isotonic agents, suspending agents, emulsifiers, stabilizers, preservatives, etc.) may be included.

The above preparations may be prepared by conventional mixing, granulating, or coating methods, and the active ingredients may be contained in an amount of about 0.1 wt % to about 75 wt %, and preferably, about 1 wt % to about 50 wt %. The unit formulation for mammals with a body weight of about 50 kg to 70 kg may contain the active ingredients in an amount of about 10 mg to about 200 mg.

The composition of the present invention may be administered in a pharmaceutically effective amount.

As used herein, the term "pharmaceutically effective amount" refers to an amount sufficient to treat or prevent a disease at a reasonable risk/benefit ratio applicable to any medical treatment. An effective dosage level of the composition may be determined considering factors including health conditions of a patient, type of disease, severity of disease, drug activity, drug sensitivity, administration method, administration time, administration route and excretion rate, length of treatment, factors including drug(s) to be used simultaneously in combination, and other factors well known in the medical field. The composition of the present invention may be administered individually or in combination with other therapeutic agents, may be administered sequentially or simultaneously with conventional therapeutic agents, and may be administered once or multiple times. It is important to administer the composition in an amount to obtain the maximum effect with a minimum amount without adverse effects considering all of the factors described above, and the pharmaceutically effective amount can easily be determined by one of ordinary skill in the art.

A preferred dose of the compound of the present invention may vary depending on the health conditions and body weight of a patient, severity of illness, drug type, administration route, and duration, but the preferred dose may be appropriately selected by one of ordinary skill in the art. For desirable effects, the compound of the present invention may be administered daily in an amount of 0.0001 mg/kg to 100 mg/kg (body weight), preferably 0.001 mg/kg to 100 mg/kg. The administration may be performed once daily or in several divided doses per day via an oral or parenteral route.

Furthermore, the present invention provides a method for preventing or treating inflammatory diseases or the diseases caused by oxidation, which includes administering the pharmaceutical composition to a subject in need thereof.

As used herein, the term "subject" refers to all animals including humans, monkeys, cows, horses, sheep, pigs, chickens, turkeys, quails, cats, dogs, mice, rats, rabbits, and guinea pigs, which have or are at the risk of developing the above diseases. The above diseases can be effectively prevented or treated by administering the pharmaceutical composition of the present invention to a subject. The pharmaceutical composition of the present invention may be administered in combination of conventional therapeutic agents.

As used herein, the term "administration" refers to provision of a particular material to a patient by an appropriate method and the composition of the present invention may be administered by any of the conventional routes, as long as it enables the delivery of the composition to the target tissue. The pharmaceutical composition of the present invention may be administered via intraperitoneal, intravenous, intramuscular, subcutaneous, intradermal, oral, local, intranasal, intrapulmonary, or intrarectal administration, but the administration method is not limited thereto. Additionally, the pharmaceutical composition of the present invention may be administered using any device that can transport an active material to a target cell.

Preferred administration methods and preparations may include those for intravenous injection, subcutaneous injection, intradermal injection, intramuscular injection, intravenous infusion, etc. Injections may be prepared using an aqueous solvent (e.g., saline, ringer solution, etc.); a nonaqueous solvent (e.g., vegetable oil, high grade fatty acid ester (e.g., ethyl oleate, etc.), alcohols (e.g., ethanol, benzyl alcohol, propylene glycol, glycerin, etc.), etc. Injections may include a pharmaceutically acceptable carrier such as a stabilizer for preventing deterioration (e.g., ascorbic acid, sodium bisulfite, sodium pyrosulfite, BHA, tocopherol, EDTA, etc.), an emulsifier, a buffer for pH adjustment, a preservative for preventing microbial growth (e.g., phenylmercury nitrate, thimerosal, benzalkonium chloride, phenol, cresol, benzyl alcohol, etc.).

The present invention provides an anti-inflammatory or anti-oxidative cosmetic composition containing the compound of Formula 1 above, an isomer thereof, or a cosmetically acceptable salt of the compound or its isomer.

As used herein, the term "anti-inflammatory" refers to an action of inhibiting inflammation. The regulation of an inflammatory response is known to be very complex, and it is known that the regulation of an inflammatory response is associated with strengthening of an in vivo recovery system and reduction of tissue damage. However, when an inflammatory response is maintained by repeated tissue damage or regeneration, it leads to overproduction of ROS and RNS in inflammation-associated cells, thereby resulting in permanent genetic modification of genes. As such, ROS and RNS are closely related to the inflammatory responses that regulate the action of various cells in vivo. During inflammation, large amounts of pro-inflammatory cytokines, nitric oxides (NOs), and prostaglandins E2 (PGE2) are produced by inducible nitric oxide synthase (iNOS) and cyclooxygenase-2 (COX-2). Inflammation is a cause of various inflammatory diseases, and a composition containing the compound of the present invention may have effects of preventing and ameliorating various inflammatory diseases through anti-inflammatory actions.

As used herein, the term "anti-oxidative" refers to an action of inhibiting oxidation. The human body maintains a balance between pro-oxidants and anti-oxidants. However, when the balance of the body is disrupted by various factors and the body is inclined toward a direction of promoting oxidation, it results in inducing oxidative stress thereby causing potential cellular damage and pathological disease. Reactive oxygen species (ROS), which is a direct cause of oxidative stress, are unstable and highly reactive. Therefore, they can easily react with various biomaterials and attack the polymers in the body, causing irreversible damage or mutations, cytotoxicity, carcinogenesis, etc. to cells and tissues. The reactive nitrogen species (RNS), such as NO, $HNO_2$, and $ONOO^-$, are produced in large amounts due to the immune response of macrophage neutrophils and other immune cells during an inflammatory response, and at this time, ROS are also produced as well. Such ROS can oxidize and destroy cells in the body, thereby exposing them to various diseases. Therefore, when the compound of the present invention is included in cosmetics, the cosmetics will be provided with an anti-oxidative effect and is thereby able to contribute to improvement of health.

In the present invention, the cosmetic composition may be prepared in the form of conventional emulsion formulation or solubilized formulation. Examples of the emulsion formulation may include a nutrition emollient, a cream, an essence, etc. and examples of the solubilized formulation may include a nutrition emollient, etc. Suitable formulations may include solutions, gels, solids or kneaded anhydrous products, emulsions obtained by dispersing an oil phase in water phase, suspensions, microemulsions, microcapsules, microgranules or ionic types (liposomes), vesicles of nonionic dispersants, creams, skins, lotions, powders, ointments, sprays, or conical sticks, but the suitable formulations are not limited thereto. Additionally, the formulation may be in the form of foam or in the form of an aerosol composition further containing a compressed propellant.

The cosmetic composition may further contain a fat material, an organic solvent, a solubilizer, a thickening agent and a gelling agent, a softening agent, an anti-oxidant, a suspending agent, a stabilizer, a foaming agent, a fragrance, a surfactant, water, an ionic or nonionic emulsifier, a filler, a sequestering agent, a chelating agent, a preservative, vitamins, a blocking agent, a humectants, an essential oil, a dye, a pigment, a hydrophilic or hydrophobic activator, a lipid vesicle, any adjuvant (e.g., any other components commonly used in cosmetic compositions), etc.

Additionally, the present invention provides an anti-inflammatory or anti-oxidative food composition, which contains the compound of Formula 1 above, an isomer thereof, or a sitologically acceptable salt of the compound or its isomer as an active ingredient.

In the case where the composition of the present invention is used as a food additive, the compound may be added to foods as it is or together with other foods or food ingredients, and properly used according to a conventional method. The amount of the active ingredients may be appropriately determined according to the purpose of use (prevention, health, or therapeutic treatment), and a sitologically acceptable food additive may be further included in the composition of the present invention. Since the composition of the present invention contains a compound synthesized from a compound derived from a natural material as an active ingredient, there is no safety issue involved therein, and thus, there is no limitation on the amount of the active ingredients to be mixed.

Meanwhile, the food composition of the present invention may include any conventional food, and can be used interchangeably with the terms known in the art (e.g., functional food, health functional food, etc.).

As used herein, the term "functional food" refers to a food prepared or processed using raw materials or ingredients that have useful functional properties for the human body pursuant to the Korean Law 6727 with regard to health functional foods. The term "functional" refers to adjusting nutrients with regard to structures and functions of the human body and obtaining useful effects for health use (e.g., physiological action, etc.).

Additionally, the term "health functional food" refers to a food having a particular ingredient as a raw material for the purpose of health supplementation or prepared or processed by a method of extraction, concentration, purification, mixing, etc. of a particular ingredient contained in a food raw material; and refers to a food that is designed and processed to exhibit a body-regulating function (e.g., body defense, regulation of biorhythm, prevention of and recovery from disease, etc.). The health functional food composition can perform the functions associated with disease prevention and recovery from disease.

There is no limitation on the type of foods in which the composition of the present invention can be used. Additionally, the composition containing the compound of the present invention as an active ingredient may be prepared with an appropriate supplemental ingredient and additive known in the art, which can be contained in the food by the selection of one of ordinary skill in the art. Examples of the foods in which the composition of the present invention can be added may include meats, sausages, breads, chocolates, candies, snacks, cookies, pizzas, ramens, other noodles, gums, dairy products including ice cream, various kinds of soups, beverages, teas, drinks, alcoholic beverages, vitamin complexes, etc. The composition of the present invention may be added, as one component, to extracted juice, teas, jellies, and juices, which were prepared by adding the compound according to the present invention.

Additionally, the foods applicable to the present invention may include special nutrient foods (e.g., milk formulas, foods for infants and young children, etc.), processed meat products, fish products, tofu, jelled foods, noodles (e.g., ramen noodles, noodles, etc.), dietary supplements, seasoned foods (e.g., soy sauce, soybean paste, red pepper paste, mixed paste, etc.), sauces, confectionery (e.g., snacks), milk products (e.g., fermented milk, cheese, etc.), other processed foods, kimchi, pickled foods (e.g., various kinds of kimchi, pickled vegetables, etc.), beverages (e.g., fruit drinks, vegetable beverages, soy bean milk, fermented beverages, etc.), natural seasonings (e.g., ramen soup base, etc.), etc., and all other kinds of foods.

In the case where the health functional food composition of the present invention is used in the form of a drink, as is the case with the conventional drink, it may further contain various sweetening agents, flavoring agents, natural carbohydrates, etc. as additional ingredients. In addition thereto, the health functional food composition of the present invention may contain nutrients, vitamins, electrolytes, flavoring agents, colorants, pectic acid and its salt, alginic acid and its salt, organic acids, protective colloidal thickeners, pH-adjusting agents, stabilizers, preservatives, glycerin, alcohols, carbonating agents used in a carbonated drink, etc. In addition, the health functional food composition of the present invention may also contain fruit flesh that may be used for preparing natural fruit juice, fruit juice drinks, and vegetable drinks.

For example, the compositions of the present invention can exhibit an anti-inflammatory effect by inhibiting the production of nitrogen oxides. Additionally, the compositions of the present invention can exhibit an anti-oxidative effect by inhibiting the release of lactate dehydrogenase (LDH).

Meanwhile, the compound of the present invention may be present in the form of a salt, in particular, a pharmaceutically acceptable salt, a cosmetically acceptable salt, or a sitologically acceptable salt. As the salt, those salts which are commonly used in the art (e.g., acid addition salts formed by a pharmaceutically acceptable free acid) may be used without limitation. As used herein, the terms "pharmaceutically acceptable salt", "cosmetically acceptable salt", and "sitologically acceptable salt" refer to any and all organic or inorganic acid addition salt of the compound, which has a concentration that is relatively non-toxic and harmless to subjects, and the side effects caused by this salt do not deteriorate the beneficial effects of the compound represented by Formula 1.

The acid addition salt may be prepared by a conventional method, for example, a method where a compound is dissolved in an excess of an aqueous acid solution, and the salt is precipitated using a water-miscible organic solvent (e.g., methanol, ethanol, acetone, or acetonitrile), and thereby an acid addition salt is prepared. An equimolar amount of the compound and an acid or alcohol in water (e.g., glycol monomethyl ether) are heated, and subsequently, the mixture may be evaporated to dryness or the precipitated salt may be filtered off with suction.

In particular, as free acids, both organic and inorganic acids may be used, for example, inorganic acids (e.g., hydrochloric acid, phosphoric acid, sulfuric acid, nitric acid, tartaric acid, etc.) and organic acids (e.g., methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic aicd, glutaric acid, glucuronic acid, aspartic acid, ascorbic acid, carbonic acid, vanillic acid, hydroiodic acid, etc.) may be used, but the free acids are not limited thereto.

Additionally, pharmaceutically, cosmetically, or sitologically acceptable metal salts may be prepared using a base. An alkali metal salt or alkali earth metal salt may be prepared, for example, by dissolving a compound in an excess amount of an alkali metal hydroxide or alkali earth metal hydroxide solution, filtering an insoluble salt of the compound salt obtained therefrom, and evaporating the filtrate, followed by drying. In particular, as the metal salts, it is appropriate that sodium, potassium, or calcium salts be prepared from the pharmaceutical, cosmetical, or sitological aspect, but the metal salts are not limited thereto. Additionally, a silver salt may be prepared corresponding thereto may be obtained by reacting an alkali metal or alkali earth metal salt with an appropriate silver salt (e.g., silver nitrate).

Unless otherwise indicated, a pharmaceutically acceptable salt of the compound of the present invention may include a salt with an acidic or basic group that can be present in the compound of Formula 1 above. For example, the pharmaceutically, cosmetically, or sitologically acceptable salts may include sodium, calcium, or potassium salts of a hydroxyl group, etc., and other pharmaceutically acceptable salts of an amino group may include hydrobromide, sulfate, hydrogen sulfate, phosphate, hydrogen phosphate, dihydrogen phosphate, acetate, succinate, citrate, tartrate, lactate, mandelate, methanesulfonate (mesylate), p-toluenesulfonate (tosylate), etc., and they can be prepared by a preparation method known in the art.

Additionally, the compound of Formula 1 above according to the present invention includes without limitation not only a pharmaceutically acceptable salt of the compound, but also solvates (e.g., possible hydrates which may be prepared from the compound) and all possible stereoisomers thereof. The solvates and the stereoisomers of the compound of Formula 1 above may be prepared from the compound of Formula 1 above using methods known in the art.

Additionally, the compound represented by Formula 1 above according to the present invention may be prepared in a crystalline or non-crystalline form, and may be optionally hydrated or solvated when prepared in a crystalline form. In the present invention, a compound containing water in various amounts as well as the stoichiometric hydrate of the compound of Formula 1 above may be included. The solvate of the compound represented by Formula 1 above according to the present invention includes both the stoichiometric hydrate and the non-stoichiometric hydrate.

DETAILED DESCRIPTION OF THE INVENTION

Hereinafter, the present invention will be described in more detail with reference to the following Examples. However, these Examples are for illustrative purposes only and the scope of the invention is not limited by these Examples.

EXAMPLE 1

Synthesis of Compound—1

A magnetic bar was placed in an eppendorf tube, and an aqueous solution in which S-allyl-L-cysteine (SAC) and N-acetyl-L-cysteine (NAC) were dissolved in the same equivalent was added to the eppendorf tube. The reaction was performed by irradiating light with 365 nm using a UV-LED curing system while stirring. In particular, the reaction temperature was set at 25° C.

The reacted material was completely dissolved by sufficiently adding tertiary distilled water thereto, and the mixture was filtered with a 0.2 μm PVDF filter, and 50 μL of the filtrate was collected and analyzed by high-performance liquid chromatography (HPLC) (Alliance 2960, Waters, Milford, Mass., USA). In the separation process, a column (length: 250 mm, inner diameter: 4.6 mm) filled with 5 mm particle size Inspire C18 (Dikma Technologies Inc., Lake Forest, Calif., USA) was used. In addition, an acetonitrile solution containing 0.1% formic acid was used as the developing solution, and the concentration of the developing solution started at 4.5%, increased to 5% at 8 minutes, to 50% at 20 minutes, and increased to 100% at 21 minutes, and then maintained thereat for 3 minutes. Then, the concentration of the developing solution was decreased again to 6% at 25 minutes and maintained thereat for 6 minutes. The detection wavelength was set at 195 nm, the flow rate of the developing solution was set at 1.0 mL/min, and the temperature of the column was set at 40° C. Two compounds according to the present invention were each obtained at retention times of 6 and 12.5 minutes, respectively. The above process was repeated several times and thereby reproducible results were obtained.

The obtained compounds were identified by measuring the UV-Vis absorption spectrum, the UPCL-ESI-MS spectrum, the IR spectrum, and the $^1$H-NMR and $^{13}$C-NMR spectra. As a result, it was confirmed that the compound recovered at the retention time of 6 minutes in the separation process using HPLC was 2-acetamido-3-(3-(2-amino-2-carboxyethylthio)propylthio)propanoic acid (indicated as "Newcompound-1") and the compound recovered at the retention time of 12.5 minutes was 2,14-dioxo-6,10-dithia-3,13-diazapentadecan-4,12-dicarboxylic acid (indicated as "Newcompound-2").

EXAMPLE 2

Synthesis of Compound—2

(1) Boc Protection by L-cysteine methyl ester

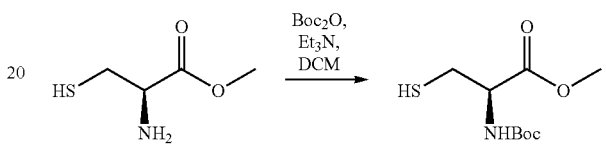

The starting material shown in the reaction scheme above, DCM (14 mL), and Et$_3$N (1 eq, 2.913 mmol, 0.4 mL, 0.726 density) were sequentially added into Rbf, and the mixture was stirred for 10 minutes while leaving a needle placed therein. Then, a solution of Boc$_2$O dissolved in DCM was added dropwise to the stirred solution. The reaction was confirmed by anis color development (EA: Hex=1:2). When the starting material disappeared, the solvent was evaporated. The compound obtained by column chromatography (MC: MeOH solvent) separation was identified by NMR.

As a result, it was confirmed that 563.3 mg of the product was obtained (yield: 82%), and NMR analysis confirmed the formation of the desired compound.

$^1$H-NMR (CDCl$_3$, 400 MHz) δ5.46 (m, 1H), 4.61 (m, 1H), 3.79 (s, 3H), 3.07-2.88 (m, 2H), 1.58-1.34(m, 10H)

(2) Reaction Between N-Boc L-cysteine methyl ester and 1,3-dibromopropane

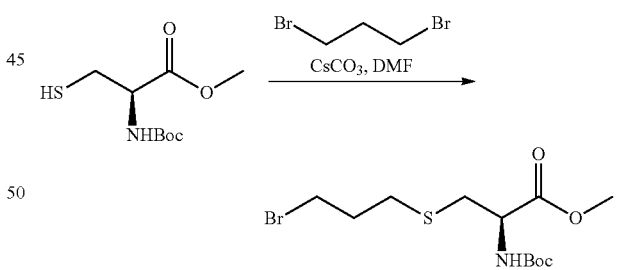

The starting material shown in the reaction scheme above, CsCO$_3$ (2 eq, 4.786 mmol, 1559 mg), DMF (15 mL), and 1,3-dibromopropane (6 eq, 14.36 mmol, 1.5 mL, density: 1.977) were sequentially added into Rbf and stirred with argon gas. The reaction was confirmed by anis color development (EA: Hex=1:4). When the starting material disappeared, the resultant was quenched with water, extracted with ether, treated with MgSO$_4$, filtered, and evaporated. The compound obtained by column chromatography (EA: Hex solvent) separation was identified by NMR.

As a result, it was confirmed that 635 mg of the product was obtained (yield: 74%), and NMR analysis confirmed the formation of the desired compound.

¹H-NMR (CDCl₃, 400 MHz) δ5.37 (m, 1H), 4.55 (m, 1H), 3.78 (s, 3H), 3.50 (t, 2H, J=6.4 Hz), 3.05-2.90 (m, 2H), 2.69 (t, 2H, J=6.9 Hz), 2.10 (p, 2H, J=6.6 Hz), 1.46 (s, 9H)

(3) Methyl Esterification Process of N-acetyl-L-cysteine

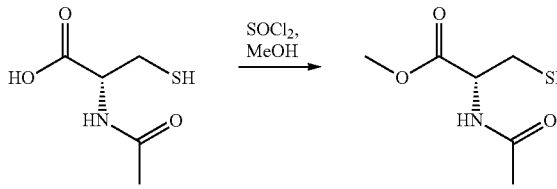

N-acetyl-L-cysteine (1 eq, 6.13 mmol, 1000 mg) (i.e., starting material) and MeOH (20 mL) were added into Rbf, and the mixture was stirred while leaving a needle placed therein, and SOCl₂ was added dropwise to the stirred solution. The reaction was confirmed by anis color development (MC:MeOH=1:20). When the starting material disappeared, the solvent was evaporated, and the resultant was subjected to EA extraction with salt water, treated with MgSO₄, filtered, and evaporated. The compound obtained by column chromatography (MC: MeOH solvent) separation was identified by NMR.

As a result, it was confirmed that 748 mg of the product was obtained (yield: 69%), and NMR analysis confirmed the formation of the desired compound.

¹H-NMR (MeOD, 400 MHz) δ4.41 (m, 1H), 3.53 (s, 3H), 2.68 (qd, 2H, J=4.9, 14.1 Hz), 1.80 (s, 3H)

(4) N-Boc Cysteine Backbone and Reaction with N-acetyl-L-cysteine methyl ester

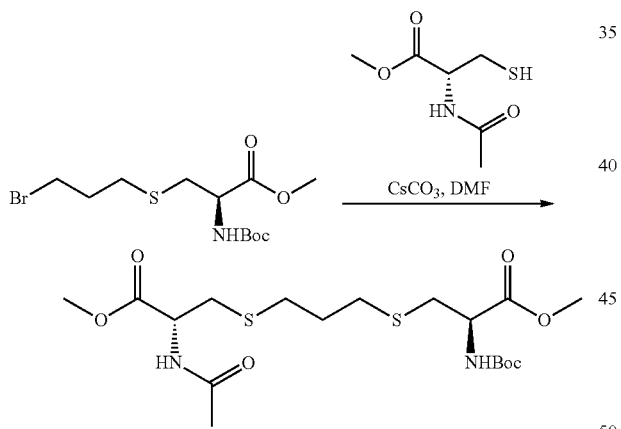

The starting material shown in the reaction scheme above, N-acetyl-L-cysteine methyl ester (1 eq, 0.255 mmol, 45 mg), CsCO₃ (1.2 eq, 0.306 mmol, 100 mg), and DMF were sequentially added into Rbf and stirred with argon gas for 10 minutes. Then, a solution of N-boc cysteine backbone (1 eq, 0.255 mmol, 91 mg) dissolved in DCM was added dropwise to the stirred solution.

The reaction was confirmed by anis color development (MC:MeOH=20:1). When the starting material disappeared, the resultant was quenched with water, extracted with Et₂O, treated with MgSO₄, filtered, and evaporated. The compound obtained by column chromatography (EA:Hex solvent) separation was identified by NMR.

As a result, it was confirmed that 47.5 mg of the product was obtained (yield: 41%), and NMR analysis confirmed the formation of the desired compound.

¹H-NMR (CDCl₃, 400 MHz) δ6.47 (m, 1H), 5.44 (m, 1H), 4.83 (m, 1H), 4.53 (m, 1H), 3.77 (s, 6H), 3.05-2.90 (m, 4H), 2.65-2.57 (m, 4H), 2.06 (s, 3H), 1.82 (p, 2H, J=7.0 Hz), 1.45 (s, 9H)

(5) Boc Deprotection using TFA

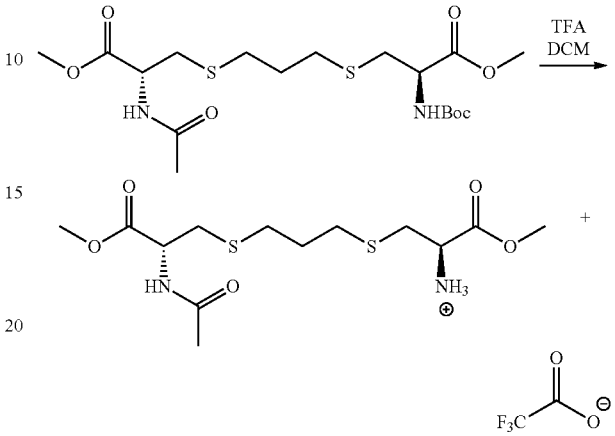

The starting material shown in the reaction scheme above (1 eq, 0.102 mmol, 46 mg), DCM (0.5 mL), and TFA (0.5 mL, density 1.489) were added into Rbf and stirred while leaving a needle placed therein. The reaction was confirmed by ninhydrin color development (MC:MeOH:AcOH=10:1:0.1). When the starting material disappeared, the solvent was evaporated and subjected to vacuum treatment. The separated compound was identified by NMR.

As a result, it was confirmed that 41.3 mg of the product was obtained (yield: 87%), and NMR analysis confirmed the formation of the desired compound.

¹H-NMR (MeOD, 400 MHz) δ4.54 (m, 1H), 4.22 (m, 1H), 3.77 (s, 3H), 3.65 (s, 3H), 3.07 (m, 1H), 2.99-2.87 (m, 2H), 2.73 (m, 1H), 2.64-2.56 (m, 4H), 1.92 (s, 3H), 1.78 (p, 2H, J=8.0 Hz)

(6) Deprotection using 2N—HCl

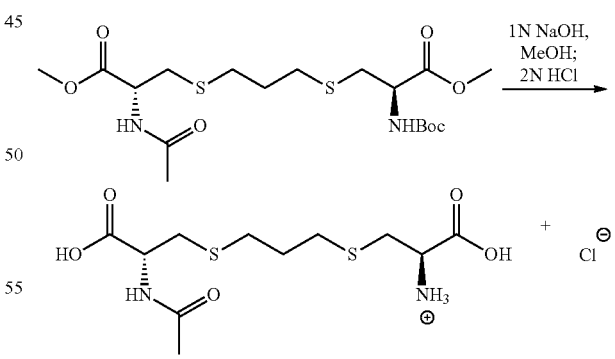

The starting material shown in the reaction scheme above (1 eq, 0.124 mmol, 56.1 mg) and MeOH (1 mL) were added into Rbf and 1 N MeOH (1 mL) was added dropwise thereto on an ice bath. The reaction was confirmed by anis color development (MC:MeOH:AcOH=10:1:0.1). When the starting materials disappeared, the resultant was quenched with 2 N HCl. The resultant was adjusted to a pH 2.0 and extracted with EA to prevent a reverse reaction.

EXPERIMENTAL EXAMPLE 1

Anti-Inflammatory Effect

Raw 264.7 cells were plated in each of 12-well plates at a cell density of $1\times10^4$ cells/well, treated with the drug to be tested at a predetermined concentration, and maintained thereat for 1 hour. The resultant was treated with LPS (100 ng/mL), cultured in a $CO_2$ incubator for 24 hours, and the concentration of NO production was measured using the Griess reagent. As the test drug, two kinds of compounds according to the present invention (indicated as "Newcompound-1" and "Newcompound-2", respectively) were used. As the comparative group, SAC and NAC (i.e., the raw materials of the compounds of the present invention) were used, respectively. As the negative control group, a group which was not treated with anything was used. As the positive control group, a group treated with LPS (LPS), where NO production was induced by treating with LPS alone, was used. SAC, NAC, and the two kinds of compounds were each treated at a concentration of 1 µM and 10 µM, respectively, and thereby a concentration-dependent effect was confirmed. The results are shown in FIG. 11.

As shown in FIG. 11, the SAC and NAC treated groups, which were used as the comparative groups, were shown to inhibit NO production by 15% to 18% and by 4% to 20%, respectively, compared to the positive control group. The compounds of the present invention showed an improved inhibitory effect by 24% to 38% and by 24% to 35%, respectively, compared to the comparative groups.

EXPERIMENTAL EXAMPLE 2

Anti-Oxidative Effect

To confirm the anti-oxidative effect of the compounds according to the present invention, the amount of lactate dehydrogenase (LDH), which is a material released from cells killed or damaged by oxidation, was measured by measuring the absorbance using water soluble tetrazolium salt (WST) to measure cytotoxicity. Specifically, Raw 264.7 cells, in which oxidation was induced with 100 µg/mL of oxidized low-density lipoprotein (Ox-LDL), were treated with test materials (2 kinds of comparative groups and 2 kinds of experimental groups) at 1 µM and 10 µM concentrations, respectively, and their ability to inhibit LDH release (i.e., a standard indicator of anti-oxidative effects) was confirmed. As reference, the LDH release rate in the negative control group in which no treatment was made was 7% and the LDH release rate in the positive control group treated with only Ox-LDL was 30%. The measurement results are shown in FIG. 12.

As shown in FIG. 12, both the two kinds of comparative groups and the two kinds of experimental groups showed reduced LDH release rates, compared to the positive control group, and the degree of decrease was increased depending on the concentration of the treated compounds. Specifically, in the case of SAC, when treated at 1 µM and 10 µM concentrations, respectively, the LDH release rate was decreased by 7% and 16%, respectively, compared to the positive control group; whereas in the case of NAC, when treated at the same concentrations above, the LDH release rate was decreased by 6% and 13%, respectively, compared to the positive control group. Meanwhile, Newcompound-1 and Newcompound-2, which are the compounds according to the present invention, when treated each at 1 µM and 10 µM concentrations, showed a decrease of LDH release rate by 12% and 21% and by 11% and 20%, respectively, and these results suggest that the compounds according to the present invention have an excellent anti-oxidative effect.

The invention claimed is:

1. A compound of the following Formula 1, an isomer thereof, or a pharmaceutically acceptable salt of the compound or its isomer:

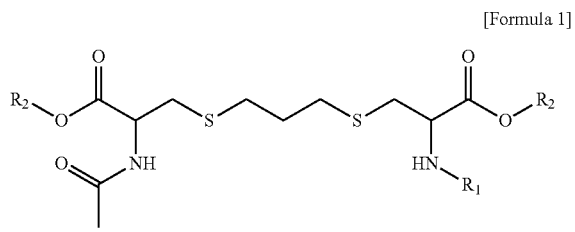

[Formula 1]

wherein in Formula 1 above,
$R_1$ is hydrogen or acetyl; and
$R_2$ is hydrogen or methyl.

2. A method for preparing the compound of claim 1, comprising irradiation of an aqueous solution containing S-allyl-L-cysteine and N-acetyl-L-cysteine with ultraviolet light.

3. The method of claim 2, wherein the ultraviolet light has a wavelength in the range of 330 nm to 400 nm.

4. The method of claim 2, wherein the irradiation is performed at 15° C. to 35° C.

5. A method for preparing the compound of of claim 1, comprising:
  (a) introducing a protecting group into the amine group of L-cysteine methyl ester;
  (b) reacting the product of Step (a) with 1,3-dihalopropane; and
  (c) reacting the product of Step (b) with N-acetyl-L-cysteine methyl ester.

6. The method of claim 5, wherein N-acetyl-L-cysteine methyl ester is produced by methyl esterification of N-acetyl-L-cysteine.

7. The method of claim 5, further comprising Step (d) to deprotect the amine group after Step (c).

8. The method of claim 7, wherein the deprotection is performed by sequentially reactions with a base and an acid.

9. A method for treating inflammatory diseases, comprising administering to a subject in need thereof a pharmaceutically effective amount of the anti-inflammatory pharmaceutical composition containing a compound of claim 1, an isomer of the compound, a pharmaceutically acceptable salt of the compound, or an isomer of the salt as an active ingredient, wherein the anti-inflammatory effect is achieved by inhibiting the production of nitrogen oxides.

10. A method for treating diseases caused by oxidation, comprising administering to a subject in need thereof a pharmaceutically effective amount of the anti-oxidative pharmaceutical composition containing a compound of claim 1, an isomer of the compound, a pharmaceutically acceptable salt of the compound, or an isomer of the salt as an active ingredient, wherein the antioxidation effect is achieved by inhibiting the release of lactate dehydrogenase.

* * * * *